(12) United States Patent
Chang et al.

(10) Patent No.: US 7,652,203 B2
(45) Date of Patent: Jan. 26, 2010

(54) ANIMAL FEED WITH LOW PHYTIC ACID, OIL BURDENED AND PROTEIN LADEN GRAIN

(75) Inventors: Ming-Tang Chang, Ames, IA (US); Peter L. Keeling, Ames, IA (US); Edward P. Wilhelm, Ames, IA (US); Jerry C. Weigel, Raleigh, NC (US)

(73) Assignee: BASF Plant Science GmbH (DE)

( * ) Notice: Subject to any disclaimer, the term of this patent is extended or adjusted under 35 U.S.C. 154(b) by 538 days.

(21) Appl. No.: 11/151,129

(22) Filed: Jun. 13, 2005

(65) Prior Publication Data

US 2005/0246791 A1    Nov. 3, 2005

Related U.S. Application Data

(60) Continuation of application No. 10/883,945, filed on Jul. 2, 2004, now Pat. No. 7,087,261, which is a division of application No. 09/477,371, filed on Jan. 6, 2000, now Pat. No. 6,774,288, which is a continuation of application No. PCT/US98/13685, filed on Jul. 7, 1998.

(60) Provisional application No. 60/051,854, filed on Jul. 7, 1997, provisional application No. 60/051,855, filed on Jul. 7, 1997.

(51) Int. Cl.
*A01H 5/00* (2006.01)
*A01H 5/10* (2006.01)

(52) U.S. Cl. .................................... 800/320.1; 800/260

(58) Field of Classification Search ....................... None
See application file for complete search history.

(56) References Cited

U.S. PATENT DOCUMENTS 5,689,054 A * 11/1997 Raboy ........................ 800/320

* cited by examiner

*Primary Examiner*—Cynthia Collins
(74) *Attorney, Agent, or Firm*—Debra L. Blair

(57) ABSTRACT

The present invention provides grain, seed, feed made from the grain or seed, pet food made from the grain, and food products made from the grain. The grain may be maize grain with the following characteristics: oil burdened, elevated protein content, and low phytate levels. The combination of oil burdened, protein laden, and decreased phytate characteristics in grain makes a grain that provides more calories, protein and phosphorus and other nutrients to the feeding animal. Pet foods, and animal feeds and corn food products made of the present invention will provide increased nutrition because of the increased bioavailability of the components of the grain.

7 Claims, 1 Drawing Sheet

ANIMAL FEED WITH LOW PHYTIC ACID, OIL BURDENED AND PROTEIN LADEN GRAIN

This application is a continuation of U.S. patent application Ser. No. 10/883,945, filed Jul. 2, 2004 now U.S. Pat. No. 7,087,261, which is a divisional of U.S. patent application Ser. No. 09/477,371, filed Jan. 6, 2000 and now U.S. Pat. No. 6,774,288, which is a continuation of PCT/US98/13685, filed on Jul. 7, 1998, which is based on and claims benefit to U.S. Provisional application Ser. Nos. 60/051,854 and 60/051,855 filed Jul. 7, 1997, the entire contents of which are incorporated herein by reference.

FIELD OF INVENTION

Broadly, the present invention relates to grain having increased oil and increased protein and amino acids, increased total phosphorus bioavailability and decreased phytic acid. This grain can be used as feedstuffs for animals. More particularly, this invention relates to grain based feed that provide improved animal nutrition, and reduces the environmental impact of animal production.

BACKGROUND

Over the last fifty years, approaches toward providing animal nutrition have changed. No longer are the animals fed whatever grain or forage may be available. Instead, the diets of animals are closely monitored for total nutrition value, and for cost. The animal on the diet is monitored, for quality and performance characteristics, and for the environmental impact of the waste from the animal. The information gathered is employed to adjust the feed to increase nutrition value of the feed and the animal performance characteristics while decreasing the cost and environmental impact.

Cereals and fats are used in feeding programs for nonruminants such as swine and poultry to provide a nutritional source of calories. The ratio of cereals to supplements, such as vitamins, minerals and fats, have changed across years in an attempt to maximize feeding efficiency of the animals. The feeding efficiency (the feed conversion ratio) or how much feed is required to produce one pound of animal weight is determined by a combination of matching the genetic potential of the animal, and the nutrients supplied to the animal. As the feed conversion ratio has risen due to genetic enhancements, the mineral nutrient requirements in the feed have risen to assure a complete and heathy diet.

Since an animal's ability to feed limits the amount of nutrients and calories it can consume, the feed industry has had to develop ways to make feeds that are more highly caloric. To increase the caloric density of the feed, producers have added fat to the feed. Fat has often been added to the feed in the form of a liquid. Fat has the advantage of supplying calories to each mouthful of feed. However, adding fat to feed has some disadvantages such as costs, added labor and technical difficulties with automatic feeding systems. Additionally, the fat is often of poor quality, thus reducing the overall quality of the feed.

To reduce the use of liquid fat in feeds, the industry has tried increasing the oil content of the grain used in the feeds. The Dupont company has developed and commercialized high oil corn as a method for increasing the oil content of feed. Other companies have developed corn that has more oil than no. 2 yellow dent corn but less than Dupont's high oil corn. High oil and elevated oil corn is herein alternatively referred to as oil burdened corn. This extra oil in the corn reduces and may eliminate the need for the addition of the liquid fat to the feed.

Traditionally, oil burdened corn has been thought to contain increased level of phytic acid, as compared with levels in No. 2 yellow dent corn. Raboy et al (Journal of Heredity 1989: 80: 311-315) have reported however, that there is an apparent negative relationship between selection for oil and total phytic acid, phytic acid phosphorus and phosphorus per kernel, per germ and per endosperm of Illinois High Oil and Low Oil lines, as opposed to the previously expected apparent positive relationship on a concentration basis (i.e., mg constituent per g kernel, germ or endosperm). Raboy explains that the discrepancy between total contents per organ and concentration per organ results from the large divergence in organ dry weights exhibited between the Illinois High Oil (IHO) and Illinois Low Oil (ILO) seed used in his study; IHO germ being about twice the dry weight of ILO germ and ILO endosperm having nearly three times the dry weight of IHO endosperm. In contrast to this trend for high oil being linked to lower phytic acid, Raboy also reports a consistent positive relationship between increasing protein selection and increasing amounts of phytic acid, phytic acid phosphorus and phosphorus. Thus, there is an apparent positive relationship between selection for protein and total phytic acid, phytic acid phosphorus and phosphorus per kernel, per germ and per endosperm of illinois high protein and low protein lines. This was maintained even when the data are expressed on a concentration basis (i.e., mg constituent per g kernel, germ or endosperm). Thus selection for protein and oil appears to divergently affect phytate content in seed.

As reports suggest an average increase of 0.38% protein with each 1% increase in oil (Han Y. Et al., 1987 Poultry Science 66:103-111; Keshararz, Poultry Pointers, pp 6-7), it is uncertain from the art whether grains containing high oil, high protein and low phytic acid could be produced (Brewer, "Optimum® High Oil Corn Improves Poultry Rations" Poultry Digest, February/March 1998 pp 30-31). Brewer states that while high oil corn is available as of 1998, varieties which are high in oil, high in protein and high in digestible phosphorus (i.e., low in phytic acid phosphorus), have yet to be developed.

The concentration of phytic acid in grain-based diets has long been of concern to humans and animal nutritionists, because evidence has shown that phytic acid acts to form insoluble salts with nutritionally important minerals that subsequently are not absorbed in the intestine. Phytic acid (myo-inositol 1,2,3,4,5,6-hexakis (dihydrogen phosphate)) is a form of phosphorus (P) in seeds which is stored in the form of phytate salts. Phytate salts have a negative nutritional impact on the animal because phosphorus bound to phytate is not available to the animal as a source of nutrition. Moreover, the animal does not retain the minerals such as Ca, Zn and the like and these needed minerals are excreted. Finally, the animal waste contain phytate P which then contributes to the surface and ground water pollution. If the grain is used for milling purposes then the milling by-products contain phytate P which then contributes to the surface and ground water pollution.

Swine, for example, lack the digestive enzyme (phytase) required to cleave the phosphorus from the phytate molecule and thus can not readily use phytate-phosphorus. Increasing the availability of phosphorus by elimination of the phytate salts binding the phosphorus would enable a reduction in dietary total phosphorus content without jeopardizing the animal's health or production performance. Increasing the bioavailability of phosphorus results in a lower phosphorus content in the swine wastes, which is environmentally desirable.

In one attempt to release a portion of the phytate P present in maize and soybean meal the feed industry has added microbial phytase to the feed of animals. This method of dealing with phytate in the grain appears to partially decrease the phosphorus excreted by the animal. This research apparently led to further methods of degrading phytate in feed. One method includes adding an enzymatic cocktail and *Aspergillus niger* mycelium to feed. These components function to hydrolyze phytate present in the corn-soybean diet. Turkeys fed the enzymatic cocktail and the fungal mycellium showed enhanced performance and retention of P and Ca. These feed studies were planned to dephosphorylate the corn and soybean based feeds prior to consumption by the animal and thus reduce the P excreted. This method of dealing with phytate in the grain has the distinct disadvantage of adding labor and cost to the feed.

Mogen, in U.S. Pat. No. 5,593,963, describes production of a temperature stable phytase enzyme from *Aspergillus* in a corn or soy seed through genetic engineering techniques. The genetically produced phytase was designed to reduce the phytic acid content in animal feed by degrading the phytic acid being released from the grain and thus decrease the level of phosphorus excreted by the animal.

Low phytic acid mutant yellow dent corn seeds have been produced by Raboy and described in U.S. Pat. No. 5,689,054. This patent describes the discovery of a single gene, nonlethal lpa1 mutants in maize that cause the reduction of kernel phytic acid phosphorus by up to 95% over the wildtype phytic acid phosphorus levels. Raboy notes that while the mutants of his invention are phenotypically very similar to the wild-type, the mutants would need to be introduced in to a breeding program in order to introduce the low phytic acid trait in to a commercial line. Moreover, Raboy explains that the low phytic acid maize mutants of his invention are characterized by a small kernel dry weight reduction which could result in a reduction in productivity and that homozygous mutants may reduce or eliminate agronomically important characteristics. As Raboy et al (Journal of Heredity 1989) has indicated that divergent selection for high protein consistently produces higher phytic acid lines, it is unclear how the Ipa1-R and Ipa2-R mutations described in the Raboy patent in yellow dent corn will interact with genes for high-protein and oil-burdened corn seed. Thus one could not have predicted with certainty whether it would have been possible to maintain a high-protein oil burdened seed in combination with a low phytic acid mutant.

Although the feed industry has addressed both the need for more energy in the feed and the need for less phytate-phosphorus, the feed industry has not addressed the need for a method of providing, in a cost efficient manner, both the high nutrient density (i.e., high protein and high oil) and the low phytic acid in feed. There is a need to reduce the amount of phytate salts formed in feed and increase the amount of energy in feed without having to add phytase and liquid oil to feed. There remains a need, which has not been addressed, for a grain having a combination of increased protein and oil burden and low phytic acid levels. To reduce feed costs in animal production requires a nutritionally dense material that is cost-effective and environmentally friendly. Additionally, there remains a need for a feed containing an oil burdened, protein laden corn with low phytic acid levels which can be used for milling or for feed purposes.

SUMMARY OF THE INVENTION

An object of the present invention is to provide a nutrient-dense grain that contains both high levels of energy, through oil and improved amino-acid content, through protein, and low levels of phytic acid.

Another object of the present invention is to decrease the phosphate and/or phosphorus excretion of animals consuming the feed while increasing the energy levels per daily feed intake and bioavailability of minerals and other nutrients.

An object of the present invention is to provide an animal feed that contains both high levels of energy through oil and protein and low levels of phytic acid.

Still a further object of the present invention is to provide a highly nutrient dense feed source to livestock which has less phytic acid present then the same feed source when made with regular commodity corn (i.e., no. 2 yellow dent corns).

Still a further object of the present invention is to provide a high energy feed source to livestock containing sufficient supplies of any rate limiting amino acid which has less phytic acid present then the same feed source when made with regular commodity corn (no. 2 yellow dent corns).

It is another object of the invention to provide a method of reducing animal phosphorus waste and/or pollution, and subsequent algal and microbial blooms caused therefrom, which method includes feeding animals, such as pigs and chickens, the animal feed of the present invention.

In one embodiment, the present invention provides a non-lethal, mutant seed or grain of a cereal plant species, such as corn (maize), rice, barley and soy, having at least about 5% by dry weight, preferably at least about 6%, alternatively at least about 7%, oil; at least 11% by dry weight, preferably at least about 12%, alternatively at least about 13%, protein; and at least about a one third (33%) reduction in dry weight in the phytic acid amount (as measured by any of total phosphorus, phytic acid or phytic acid phosphorus), preferably at least about a one half (50%) reduction, alternatively at least about 60-70% reduction, relative to wild-type seed of said species. Where the seed of the present invention is corn, the comparison in reduction is preferably made relative to standard number (no.) 2 yellow dent corn.

In another embodiment, the present invention provides an increase in phosphorus availability of from 28% for yellow dent corn to greater than about 70%, preferably less than about 90%, alternatively about 80% to about 84-85%, availability being the amount of utilizable phosphorus compared to total phosphorus from feed. The hybrid grain of the present invention is preferably a cross between useful inbreds and an inbred line ExSeed line U095-1pa1-E (alternatively referred to as U095-E or U095py; a representative deposit of 2500 seeds of which have been deposited as strain designation EX1965py on Jul. 7, 1998 with American Type Culture Collection, 10801 University Blvd., Manassas, Va. 20110-2209 USA, under conditions of the Budapest Treaty, Accession No. 203034. Source U095-py 1656-W97-Florida-100). The deposit was made in accordance with the terms and provisions of the Budapest Treaty relating to deposit of microorganisms and was made for a term of at least thirty (30) years and at least five (5) years after the most recent request for the furnishing of a sample of the deposit is received by the depositary, or for the enforceable life of the patent, whichever is longer, and will be replaced if it becomes non-viable during that period. The "E" or "py" designation used herein indicates the introduction of an 1pa1 mutation by the present inventors.

A number of other crosses and inbreds can be employed. For example, the following female inbreds BD68py, TR306py, WD22py and TR329py were crossed with male inbreds U095py, UU01py, UE95py, TR335py and TR386py to make high-yielding hybrid combinations. Crosses with U095py are particularly preferred and the inbred U095py and hybrids made therefrom are specific embodiments of the present invention. The hybrid grain of the present invention is characterized by having ~6% oil and 12% protein (or 3% more oil and 3% more protein than yellow dent corn) and at least about 33% reduction in phytic acid content.

In another embodiment, the present invention provides a feed containing a seed, as described herein, and at least one source of vitamins or minerals, containing, for example, any one or a mixture of at least two of calcium or phosphorus or salts thereof, vitamin A, vitamin D, vitamin E, $B_{12}$, riboflavin, pantothenic acid, niacin, biotin, and trace minerals, such as iron, copper, manganese, zinc, iodine, and selenium, and/or additional feed additives, such as antibiotics, arsenicals, chemotherapeutics, flavoring, antioxidants and plant extracts; said feed providing a nutritionally balanced diet and a greater amount of biologically useful phosphorus to an animal consuming said feed than does the same feed formed with wild-type seed of the species. The feed of the present invention may also contain amino acid additives, such as lysine and methionine.

In another embodiment, the present invention provides an improved feed which is otherwise formulated for swine or poultry but includes the seed, preferably corn seed, of the present invention.

In yet another embodiment, the present invention provides a method of increasing bioavailability of phosphorus from products containing wild-type seed of a species, said method including the steps of providing a seed containing product, such as a feed as described herein, for consumption, wherein the seed containing product contains a seed of the present invention, and feeding the seed containing product to an animal which will benefit from an increased bioavailability of phosphorus.

In a further embodiment, the present invention provides germplasm which will yield the seed of the present invention. In a preferred embodiment, the present invention provides corn germplasm which will yield the corn seed described herein.

In yet another embodiment, the present invention provides a plant produced from a seed of the present invention.

In yet a further embodiment, the present invention provides a seed of the present invention which is fully mature.

Still, further objects and advantages will become apparent from a consideration of the ensuing description.

DETAILED DESCRIPTION

Figure 1:
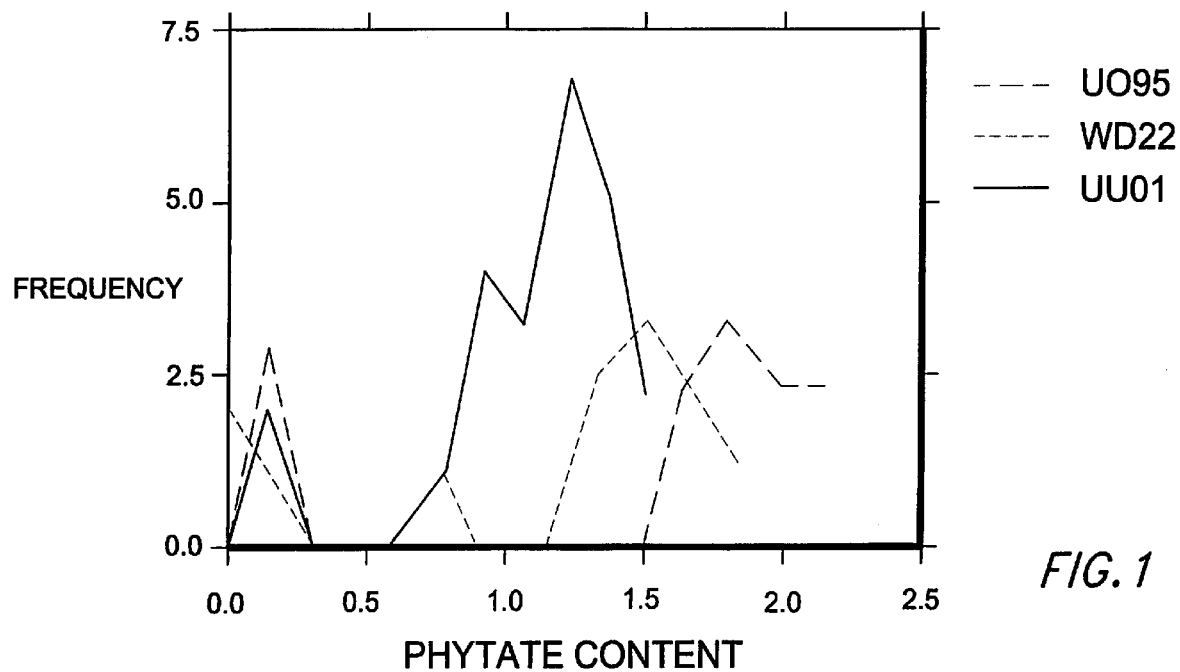
FIG. 1 shows a frequency distribution of phytate contents of screened M2 seed.

The present invention provide grain, feed made from the grain, petfood made from the grain, and food products made from the grain. The grain is preferably maize grain with the following characteristics: oil burdened, elevated protein content, and low phytate levels. The preferred grain has at least 5% oil, at least 11% protein, and at least about 20% to about 70%, preferably at least about to 33% to about 60% reduction in the phytic acid level relative to wild-type grain, such as standard yellow dent corn. More preferably the grain has at least 6%, more preferably 7% oil, at least 12%, and more preferably 13% protein, and at least a one half reduction in the phytic acid level relative to standard yellow dent corn wherein the grain is low phytate. Percentages are expressed on a dry weight basis as amount of a constituent per kernel, unless described otherwise. The combination of oil burdened, protein laden, decreased phytate characteristics in grain makes a grain that provides more calories, protein and phosphorus and other nutrients to the feeding animal. Pet foods, animal feeds and corn food products made of the present invention will provide increased nutrition because of the increased bioavailability of the components of the grain.

In other words the present invention includes an animal feed for a specific animal type. In one embodiment, the present invention provides a feed having a gross energy and at least the same ratio of performance limiting amino acids to gross energy as a nutritionally balanced feed using no. 2 yellow dent corn formulated for a similar type animal. The feed is formulated with an energy source including elevated oil, protein and low phytic acid maize. Additionally, the feed can contain at least one protein source including a potentially performance limiting amino acid component in a ratio to said gross energy such that the amino acid is not performance limiting, at least one source of vitamins and minerals; wherein the feed provides to the animal a higher calorie and lower phytic acid grain than no. 2 yellow dent corn in a nutritionally balanced feed. The limiting amino acid can be various different amino acids according to the needs of the animal species but it preferably includes lysine, tryptophan, threonine and methionine. The protein source of the feed can also include soybeans as a component. The feed of the present invention can also include the vitamins and a mineral source such as calcium, phosphorus and salt. In one embodiment, the feed of the present invention has vitamins and mineral sources which include any one or a mixture of vitamin A, E, D, $B_{12}$, riboflavin, pantothenic acid, niacin, biotin; trace minerals, such as any one or a mixture of iron, copper, manganese, zinc, iodine, selenium, and feed additives, such as are known in the art and may include any one or a mixture of antibiotics, arsanicals, chemotherapeutics, flavoring, antioxidants and plant extracts.

The present invention provides a method of increasing bioavailability of phosphorus from maize containing products comprising the steps of: providing a maize containing product for consumption, wherein said maize containing product is formed from maize grain of the present invention, such as that characterized by having at least 5% oil, at least 11% protein, and at least a one third reduction in the phytic acid level relative to standard yellow dent corn, wherein the grain of the present invention is lower in phytate concentration than standard yellow dent corn; and consuming said maize containing product which contains less phytate in the maize material than the same maize product made with yellow dent corn wherein the bioavailability of the phosphorus in said maize is increased over the same product made with yellow dent corn.

The present invention further provides a feed for any non ruminant animals. The feed of the present invention is particularly well-suited as a constituent in the diets of swine or poultry.

In another embodiment, the present invention provides an animal feed having a gross energy content for a specific animal type, said animal requiring a certain level of an amino acid in the feed to achieve good performance from said feed, the feed containing corn having an elevated amount of oil compared to the average oil levels of no. 2 yellow dent corn and low phytic acid levels compared to the average phytic acid levels of no. 2 yellow dent corn; a protein source, preferably substantially provided from the grain of the present invention; and having at least the same ratio of performance limiting amino acid to gross energy as a nutritionally balanced feed using no. 2 yellow dent corn formulated for a similar type animal.

The present invention provides grain having increased energy, protein and low phytic acid. This grain can be used as feedstuffs for animals or this grain can be milled. The present invention provides a new maize seed, plant and grain that carry the oil burdened, protein laden and the low phytic acid and the use for such new grain. The grain-based feedstuffs provide improved animal nutrition, and reduce the environmental impact of animal production. Even more particularly this invention provides an animal feed formulated using the grain of the present invention.

Many crop plants are used for the production of food for human or animal consumption, for commercial processes yielding products for human consumption, for the development of industrial products and for other purposes. Traditionally, the improvement of crop plant species involves the introduction of desired traits by genetic crosses. The present invention likewise can be made repeatedly though the use of standard crop, such as corn, breeding and mutation practices.

Corn grain is considered to be a high quality grain for use in foods and feeds. High oil corn is considered more energy dense then other corn. High oil corn presently is commercially available from Dupont. However, this corn like all corn contains phytic acid. Until the present invention low phytic acid and oil burdened, protein laden corn plants and grain did not exist. The invention also provides an improved flour from milling of the seed of the present invention. Thus, low phytate, oil burdened, elevated protein maize grain should address the need for energy, protein dense corn and mineral bioavailability within the cereal grain.

The method of repeatedly making the grain of the present invention is as follows. Generally, in the course of a maize breeding program oil burdened, protein laden corn plants are crossed with maize plants carrying the low phytic acid allele. Oil burdened corn plants can be developed by recurrent selection as evidenced by University of Illinois high oil corn (commercially available from Dupont), or from transformation (methods of transforming corn are well known to those having ordinary skill in the art). This is one part of the starting material to make the present invention. The other part is a low phytic acid plant. Although this is not commercially available, experimental material is available.

High oil grain is commercially available from Dupont as either a Top Cross grain or a high oil hybrid corn (high oil is any grain of corn having greater then 3.5% oil). Oil burdened corn is defined as corn having on average a higher percentage of total oil levels than the average standard yellow dent corn oil levels.

The following table shows the levels weight % of total oil of various oils of a number of oilseed crops. The numbers under corn are the levels in standard no. 2 dent corn.

TABLE 1

| Fatty Acid Compositions of Commercial Crops | | | | | | |
|---|---|---|---|---|---|---|
| | sun(hiO) | canol | lolinCan | Crambe | Corn | Soy |
| (C16:0) palmitic | 6 | 4 | 5 | 2 | 11 | 11 |
| (C16:1) palmitoleic | 0.3 | 0.3 | 0.4 | 0.3 | | |

TABLE 1-continued

| Fatty Acid Compositions of Commercial Crops | | | | | | |
|---|---|---|---|---|---|---|
| | sun(hiO) | canol | lolinCan | Crambe | Corn | Soy |
| (C18:0) stearic | 5 | 1.5 | 1.5 | 1 | 2 | 4 |
| (C18:1) oleic | 20 (81) | 62 | 62 | 17 | 28 | 22 |
| (C18:2) linoleic | 68 (9) | 20 | 27 | 8 | 58 | 53 |
| (C18:3) linolenic | 0.2 | 10 | 2 | 7 | 1 | 8 | sun(hiO)—sunflower high oil
canol—canola
lolinCan—low linoleic canola
Crambe
corn
soy—soybean Thus the present invention encompasses grain that is oil burdened, preferably with fatty acid compositions in the ratios listed above. The present invention also encompasses corn that has increased the fatty acid compositions such that there is not an overall increase but there is a result increase in usefulness of the material to the animal fed the altered corn. The present invention also encompasses grain that is oil burdened and the fatty acid compositions are in a different ratio than listed above.

The ratio of oils present in grain cereals can be varied though genetic mutation, selective breeding, transformation and the like. The essential grain for the feed can be produced by standard methods of production of hybrid material such as the crossing of a oil burdened, elevated protein inbred with a low phytic acid inbred to produce hybrids having the grain characteristics including the low fatty acid and the elevated oil.

As noted above, Raboy et al have reported a positive correlation between protein selection and increased levels of phytic acid in corn. The following table lists the value of the amino acids present in one type of nutrient dense corn which can be used to form the grain of the present invention. The protein in corn is controlled by many different genes. The preferred high protein corn has an increased percentage of most of the amino acids present in corn grain. One example of high protein material has been the high protein corn developed by recurrent selection in the University of Illinois. Many of the other high protein corn available have an increase in lysine and not necessarily an overall increase in most amino acids. This type of high protein is also useful as this increased protein is needed by the feeding animal for overall health and this protein is better utilized when combined with the other traits of the present invention. To facilitate the breeding of hybrid seed the high protein trait is additive or dominant. Quality protein maize includes the high protein material available from Wilson seeds and from Crows and from public depositories and universities. Alternatively, high protein material can be generated by recurrent selection or by the use of certain mutation in corn like o2:su2 which have 49% more lysine then normal hybrids but have decreased protein yields. In development of the present invention a high protein trait that was additive and increased most protein levels beyond average yellow dent corn was used. Protein laden corn shall refer to corn that has increased amino acid content when compared to average amino acid content of yellow dent corn, and/or differing ratios of amino acid contents when compared to average amino acid content of yellow dent corn. High protein corn shall refer to corn that has increased amino acid content when compared to average amino acid content of yellow dent corn.

TABLE 2

Yellow-dent vs. EX404
(EX404 has ~1% wt % more oil and ~2-3% wt % more protein then does standard yellow dent corn (average 3-3.5% by weight oil and 7-9% by weight protein) EX404 and ES404 as used herein are the same)
Amino Acid Composition:

|  | Dent | ES404 | % change |
|---|---|---|---|
| TRYPTOPHAN | .06 | .06 | 100% |
| ASPARTIC ACID | .57 | .83 | 146% |
| THREONINE | .29 | .47 | 162% |
| SERINE | .41 | .63 | 154% |
| GLUTAMIC ACID | 1.52 | 1.89 | 124% |
| PROLINE | .74 | 1.04 | 141% |
| GLYCINE | .33 | .41 | 124% |
| ALANINE | .63 | .87 | 138% |
| CYSTEINE | .18 | .24 | 133% |
| VALINE | .38 | .47 | 124% |
| METHIONINE | .17 | .26 | 152% |
| ISOLEUCINE | .26 | .36 | 138% |
| LEUCINE | 1.01 | 1.48 | 146% |
| HISTIDINE | .24 | .35 | 145% |
| LYSINE | .24 | .31 | 129% |
| ARGININE | .29 | .42 | 107% |

This table clearly evidences that most of the the amino acid values of the nutrient dense corn are increased over the yellow dent material. This extra protein appears to be available for the animal's use when the phytic acid is substantially reduced. The ratio of proteins present in grain cereals can be varied though genetic mutation, selective breeding, transformation and the like. The present invention provides a grain containing increased levels of bioavailable protein in conjunction with increased levels of oil and reduced levels of phytic acid.

Prior to the release by the USDA of the Low Phytic Acid mutants B73 Ipa1-R, A632 Ipa1-R and selection thereof, there was only the conventional method of breeding for producing low phytic acid in corn seed. Low phytic acid in corn seed developed by standard breeding appeared to carry some undesirable agronomic traits. Due to the recessive nature of the phytic acid gene the preferred method requires that this gene be fixed in both inbreds. The mutant containing low phytic acid can be developed according to the following method. Selection for phytic levels must be carefully performed as too low a level of phytic acid may result in lethal seeds.

The low phytic acid plant of the present invention can be developed by following the listed steps which do not take undue experimentation and can be done by the ordinarily skilled person in the art of plant breeding. The best method for generating a low phytic acid maize plant employs maize pollen mutagenesis. The induced mutation in a haploid pollen grain would give rise to a heterozygous genotype in the seed. Since low phytic acid presently is known as a recessive gene, the resultant mutant seed must be planted and selfed and the resultant plants seeds assayed for the mutant phenotype. The assaying of the seed should be done when the seed is in the mature stage or harvesting stage.

Mutagenesis is effected by conventional means in the art such as irradiation, chemical treatment, and transposable element insertion. One standard procedure is taught by Neuffer et al. Maize for Biological Research, W. F. Sheridan (Ed.), Plant Molecular Biology Association (1982). This procedure uses ethyl methane sulfonate (EMS) applied to pollen. The pollen is used for pollination and the resultant seeds are planted and the seeds from the second generation can be tested for phytic acid content. The test for P has been known in the art since 1990 when the HVPE method was published in Maydica 35:383 (1990) by Raboy. The method relies on differential migration of phosphorus compounds. After electrophoretically fractionating the compounds a chromatogram allows a semi quantitative assessment of the phytic acid relative to other compounds. An alternative method involves screening for higher levels of inorganic P in the grain. For example grain samples can be ground (to pass a 2 mm screen in a Wiley mill) followed by addition of either 50 mg of grain germ or 1 gram of endosperm in 15 ml of 0.4 M HCL in 0.7 $Na_2SO_4$. Phytic acid precipitates as an iron salt. Phosphorus in the ferric phytate precipitates and total P are determined. Phytic acid P (mg) are converted to phytic acid by use of a conversion factor of 3.5. These results lead to the selection of the desired maize plants containing the desired alleles. Other methods of testing for P are known and can be used to select plants. The seed containing the desired phytic acid is then increased. This process was employed in the present invention and inbred line were selected that carried new alleles at the Ipa1 locus. These included EX404 (low phytic) which was crossed to one of the inbreds of the present invention to form a hybrid that produced the grain of the present invention. Additionally, the developed inbreds of the present invention were from stiff stalk, Lancaster and another versatile heterotic patterns so that the inbreds when crossed together with the appropriate heterotic groups formed excellent hybrid material. It was also discovered that a number of the developed mutations of the present invention, though low in phytic acid were not the same mutant as the Ipa1-R mutation as indicated by allelic testing.

The method used in the present invention can be used to form two inbreds which would be crossed to form a high yielding hybrid. Inbreds are commercially available from Universities and Foundation Seed Companies and can be made by plant breeders skilled in the art of breeding maize inbred lines. One or both of the inbreds fixed for the low phytic acid can be crossed to an inbred which carries the elevated oil trait. Either inbred can cary the high protein trait if it was selected as an additive trait. Thus allowing the hybrid combination to carry both traits the recessive low phytic acid and the dominant or additive oil genes. A corn plant is repeatedly bred until the low phytic acid allele is present in two inbreds that cross well to one another. Likewise at least one of the inbreds in the hybrid combination must contain the oil burdened trait and/or the protein laden corn alleles.

Alternatively this grain can be produced by using the crossing method of breeding taught in the Dupont patent application WO92/08341 (U.S. Pat. No. 615,839). This method requires that the male pollinating plant carries the oil burdened trait. In Dupont's method the oil pollinator which is an inbred is mixed in with hybrid seed that is male sterile. The male pollinator then forms oil burdened grain on a sturdy hybrid plant.

In the present invention the male pollinator would preferably have two traits, a fixed recessive gene for phytic acid and the oil burdened, protein laden trait. Additionally, the male sterile hybrid would have the low phytic acid trait also.

Methods of formulating an animal feed that contains additional energy, protein and low phytic acid in one grain source are herein described. The preferred method is to improve feeds or petfoods by substituting the grain of the present invention for the corn grain normally employed. Other ingredients in the feed can be milling coproducts, protein ingredients, soybean meal, trace minerals and vitamins, and other cereals and feed additives and flavorings. This feed requires that grain be produced that is characterized as having increased oil and increased protein/amino acid and low in phytic acid. Surprisingly, the combination of the low phytic acid with the oil burdened and elevated protein appears to allow the animal to utilize the extra protein that is in the oil burdened corn and the newly available phosphorus more efficiently leading to increased feed efficiencies. The grain resulting from this hybrid combination can be used in an animal feed. This feed should contain the combination of oil burdened, elevated protein and low phytic acid and other feedstuffs employed in the diets of either swine or poultry.

Preferably if other grains are used, these grains are selected to have as low a phytic acid content as is possible in that type of grain. Though the percentage of the grain as a part of the overall diet would determine how stringently the selection against phytic acid would have to be.

The present invention is of particular use for feeding non ruminant animals. The feed ingredients for the standard swine diet are provided below. The feed mixture of the present invention substitutes the grain of the present invention for the no. 2 corn. The grain having characteristics of low phytic acid and higher oil and increased amino acids. This grain, when provided to the animal, results in a higher caloric density available and a greater bioavailability of a number of nutrients such as minerals. The use of this grain in feed reduces the need for added animal fat or vegetable oils.

Swine are primarily fed a fortified corn-soybean meal diet. Piglets, pre-weaning or early weaned, often have additives in the diets such as dried milk products, and other high protein and fat sources added to the diet. A complete swine diet provides all the nutritional needs of the pig in one diet. These diets may be prepared by mixing a balanced supplement with corn: soybeans meal and a vitamin-mineral premix with corn. Conventional feeds were often supplemented with sources of supplemental fat which are plant seed oils (extracted), grease and tallow, and commercial dry fat, corn oil, soybean oil or full fatted cooked soybeans. Flowability of the diet in automated feeders was compromised at 6 percent fat. Overall 1 percent fat produced approximately 2 percent improvement in efficiency (additional weight gain per weight of feed consumed). Increased oil from the use of the present feed (employing maize grain that is elevated oil and low phytic acid) increases the caloric density of the diet bioavailability of metals and reduces undesired waste. The feed of the present invention employs the corn grain of the present invention as a substitute for the grain presently employed in diets for animals. The following two new feed combinations will employ such grain. Both of these feed uses are for animals which are preferable non ruminant animals. Such animals include swine, poultry, cats, dogs, horses, sheep and the like.

Dietary nutrient density, when increased, maximizes animal performance. This includes animals such as sheep, swine, poultry, dogs, cats and horses. This grain is primarily effective with most monogastric animals. To formulate a diet containing the grain of the present invention that contains higher levels of oil and amino acid than standard corn requires the step of substituting the grain of the present invention for the yellow dent corn (or even for the oil burdened corn) in the diet. The invention then however, requires the step of adjusting the protein to energy level of the diet according to the needs of the animal. For example if the diet is for swine then the ratio of lysine should be increased. If the diet is for poultry then the rate of methionine should be increased and likewise for each animal.

The amino acid composition of protein specifically lysine which acts as a growth limiting amino acid for swine is increased in light of increased energy levels to keep a good balance of energy verses protein when using the feed of the present invention. The invention itself increases the lysine. In the example given in table 2 of one of the maize grains containing increased oil and amino acid content the increase in Lysine is 29% over the regular maize grain. If the increase in the rate limiting amino acid in the grain of the present invention is sufficient, the diet may not require additional increases in this amino acid. However, to the extent that the grain does not carry all of the necessary amino acids if sufficient amounts to put the diet in balance, they must be added to the diet.

The following table includes ingredients that are used in a standard feed for swine. In the present invention these ingredients can likewise be used, however, the standard corn and corn products made from standard corn should be substituted by using the grain of the present invention or products made from the grain of the present invention. Preferably added fats are not required in the feed. Additionally use of low phytic legumes and other protein sources are encouraged. These examples, as others herein, are illustrative of the use of the present invention and are not intended to limit the scope of the disclosed invention.

| Energy, Fat, Protein of Typical Ingredients Used in Swine Diets | | | |
|---|---|---|---|
| Ingredient | kcal metabolizable energy/lb | protein % | fat % |
| Animal fat | 3585 | | 100 |
| Alfalfa | 775 | 17 | 3.0 |
| Barley | 1380 | 11 | 1.8 |
| Blood meal | 1060 | 86.0 | 1.0 |
| Corn, yellow | 1555 | 8.0 | 3.25 |
| Corn, gluten (ml) | 1760 | 60.0 | 1.0 |
| cottonseed meal | 1160 | 41.0 | 2.0 |
| distillers dried grain w/solubles | 1515 | 27.0 | 8 |
| fish meal | 1500 | 60.0 | 6.0 |
| Lysine hydrochloride, limestone, dicalcium phosphate | 1100 | 48.0 | 5.0 |
| Milo | 1490 | 9.0 | 2.0 |
| Molasses | 910 | 3.0 | |
| Oats | 1243 | 12 | 3.0 |
| Skimmed Milk (dried) | 1630 | 33 | 1.0 |
| Soybean meal | 1535 | 47.5 | 1.0 |
| Soybeans (fat cooked) | 1650 | 37 | 18.0 |
| Soybean Oil | 3300 | | 100.0 |
| sunflower | 1000 | 28.0 | 2.0 |
| Wheat | 1500 | 13 | 3.0 |
| Whey | 1405 | 14 | .5 |

As is clearly evidenced in articles such as Adams, K. L. and Jensen A. H. "High Fat Maize in Diets for Pigs and Sows in Animal Feed" in Science and Technology, 17 (1987) 201-212, hogs fed higher energy diets using just high oil corn (and not the present invention of oil burdened, elevated protein and low phytic acid) with an energy: lysine ratio adjusted to the animal type (ie farrowing, starter pigs, finishing pigs) showed better feed efficiency then the same type of pig on a No. 2 corn soybean diet. The present invention used on this type of pig will provide a diet that is not only calorie dense and thus increases feed efficiency but also is low in phytic acid which permits the feeding animals to absorb from the grain the trace minerals, amino acids and macro minerals needed for increased efficiency and gain. However, like the previous tests with high oil corn the pig on a diet including grain of the present invention will require the increase in nutrients from the oil burdened, elevated protein and low phytic acid grain to be balanced with an increase in the lysine level, if necessary.

Pig diets to be nutritionally balanced should have protein, amino acids, such as lysine, threonine, tryptophan, and major minerals, such as calcium, phosphorus, salt, and vitamins such as A, D, E, $B_{12}$, Riboflavin, Pantothenic acid, Niacin, Biotin and trace minerals such as iron, copper, manganese zinc, iodine, selenium. Additionally feed diets often include feed additives such as flavorings and may have some of the following chemicals added Apramycin, bacitracin, chlortetracycline, bambemycin, carbadox, lincomycin, penicillin, tylosin, virginiamycin and the like.

Another potential use (other than as petfood and feed for swine) of the feed described herein is for poultry feed. Poultry includes most domesticated fowl including duck, geese, pheasant, turkeys and chickens. The nutrient requirements of poultry and swine differ but the basic ingredients in their diets are very similar. Poultry utilizes cereal grains and grain co-products, fats and carbohydrates in their diets. The largest part of the poultry diet is made up of cereal grain. These at least include corn, wheat, oats, milo, barley. However, in accordance with the present invention the preferred main grain ingredient is oil burdened, protein laden and low phytic acid corn. The present invention envisions that little to no corn is used in the feed of the present invention that is not the grain or a product of the grain of the present invention. In addition the feed of the present invention includes proteins which may come from peanut meal, soybean meal, cottonseed meal, fish byproducts, blood meal and poultry byproducts and the like. The feed of the present invention may also include minerals and vitamins particularly calcium as limestone or oyster shells and vitamins $D_3$, choline, menadione, A, E, $B_{12}$ and feed additives such as antioxidants, antibiotics. Like swine, poultry seem to have a specific amino acid that, if deficient, will reduce the animal's performance on the feed. For poultry, the limiting amino acid is methionine while for swine the limiting amino acid is lysine. Thus, when the present invention feed is formulated there must be an increase in the amount of methionine and general protein to keep the desired protein gross energy ratio in the diet as compared to the same ratio in the diet formulated with no. 2 grain maize. Again the present invention provides not only the nutrient dense feed but increases the bioavailability of the trace metals due to the decrease in the chelating agent, phytic acid, resulting in an increase in feed efficiency of poultry on the present invention.

Although the description above contains many specificities, these should not be construed as limiting the scope of the invention but as merely providing illustrations of some of the presently preferred embodiments of this invention. Various other embodiments and ramifications are possible within its scope.

The Iowa State University extension office publication entitled "Life cycle Swine Nutrition," PM489, revised 1996 on pages 12, 15 and 20 show a number of diets for sows and boars under standard production conditions. The following information shows that pig feeds and poultry feeds for different animals life stages are know in the prior art. The following is an example of one diet for a pig at a given development stage.

EXAMPLE 1

A pig having a moderate, lean growth potential with the following weights are defined by the following stage development numbers. Pounds 6-8=stage 1, Pounds 8-13=stage 2, Pounds 13-18=stage 3, Pounds 18-26=stage 4, Pounds 26-37=stage 5, Pounds 37-51=stage 6, Pounds 51-69=stage 7, Pounds 69-91=stage 8, Pounds 91-118=stage 9, Pounds 118-150=stage 10, Pounds 150-188=stage 11, Pounds 188-233=stage 12, Pounds 233-283=stage 13.

The pig diet developed herein was formulated for a pig in stage six. A stage six pig would require for every one thousand pounds of feed: 648.4 lbs of corn, 320.0 lbs soybean meal, dehulled 8.50 lbs of limestone, 15.25 lbs. dicalcium phosphate, 4.10 lbs salt, 1.65 lbs trace mineral premix, 0.75 lbs Fat soluble vitamin premix, 0.65 lbs vitamin B premix, 0.50 lbs Biotin and Folic acid premix, 0.20 lbs choline premix and any feed additives approved by FDA. This feed is made according to the present invention by substituting the corn of the present invention into the feed instead of the no. 2 corn and increasing the level of lysine to match the increased energy in the diet to avoid the lack of lysine from limiting in the animal's growth. If the feed is pelleted then the vitamins should be increased approximately 20%.

Corn is the basic cereal grain used in animal feeds. Corn contains many of the essential nutrients that are required by the animal. The modern animal, with its tremendous genetic ability to deposit lean tissue versus fat, has a tremendous requirement for nutrients. As this demand for fat, has a tremendous requirement for nutrients, as this demand for increased nutrition, we have at the same time see a decline in feed intake, While animal genetics had and continue to improve carcass qualities by reducing total body fat, the environmentalists have indicated that our concentrated animal feeding operations are polluting the ground and subsequent groundwater. Knowing that corn is the leading feeding ingredient used in animal production the present invention is a corn that contains concentrated nutrients, and nutrients that had higher biological availability to the animal. Such nutrients include protein, energy, amino acids and minerals. The key mineral, phosphorus, is essential for growth, health and production. Phosphorus in corn is only ~30% available to the animal because of the phytic acid content of the corn. However, the nutrient dense corn of the present invention has a greater availability of the phosphorus.

EXAMPLE 2

This experiment determines the response of commercial broiler chickens to low phytic acid mutant yellow dent corn as compared to yellow dent corn.

The trials use commercial broiler chickens in a 13-day feeding study. The basal diet is an NRC (National Recommendation Committee) based corn diet. The treatment is a replacement of conventional yellow dent corn with low phytic acid hybrid grain obtained from a cross between B73 Ipa1-R and an Exseed inbred line UU01-Ipa1-E (alternatively referred to herein as UU01-E or UU01-py) which is a low phytic mutant of yellow dent corn.

All experiments were managed under the Good Laboratory Practices with animals welfare at the forefront. Feed and water is supplied ad libitum, body weight and feed intake is measured throughout the experiments, phosphorus availability is measured by means known in the art. Carcass evaluations, total body weight gain, feed conversion ratio, mortality, morbidity and intakes are reported. The expected results are improved phosphorus availability of low phytic acid yellow dent corn versus yellow dent corn.

It is believed that the grain of the present invention in the diet will result in less excreted phosphorus. This will result in less pollution.

In this study, 8 day old New Hampshire×Columbian male chicks with an average initial weight of 73.7 g were used to compare the phosphorus availability of low phytate yellow dent corn of the present invention compared to conventional corn (yellow dent). This experiment was a CRD; 7Tx4Rx5C, 13 day trial (7 treatments, 4 replications, 5 chicks per treatment).

The basal diet was as follows: cornstarch/dextrose (2:1 ratio) to 100%; soybean meal 47.4%; soybean oil 5%; Limestone 1.2%; Salt 0.35%; vitamin mix (A, $D_3$, E, K, scotin, riboflavin, pantothenic acid, niacin, choline chloride, folic acid, thiamine, $B_6$, $B_{12}$) 0.35%; mineral mix (copper, iodine, iron, manganese, selenium, zinc) 0.15%; choline 60, 0.1%; DL-Met 0.25; flavomycin 0.05%. The basal diet contained 0.1% available phosphorus, 0.63% Ca and 23% CP. All percentages are on a weight basis.

The treatment design for this trial was as follows 1: Basal diet; 2: Basal plus 0.06% phosphorus (inorganic phosphorus) from potassium phosphate ($KH_2PO_4$); 3: Basal plus 0.12% phosphorus from potassium phosphate ($KH_2PO_4$); 4: Basal plus 20% conventional corn; 5: Basal plus 40% conventional corn; 6: Basal plus 20% low phytate corn; 7: Basal plus 40% low phytate corn.

| Weight gain - 8-20 d (g) | | | | | | | |
|---|---|---|---|---|---|---|---|
| | 1 | 2 | 3 | 4 | 5 | 6 | 7 |
| R1 | 227.8 | 269.8 | 291.2 | 209.2 | 249.4 | 253.2 | 283.0 |
| R2 | 216.8* | 267.6 | 295.4 | 224.0 | 258.8 | 249.4 | 273.0* |
| R3 | 237.0 | 285.6 | 294.4 | 229.8 | 259.6 | 244.2 | 255.0 |
| R4 | 224.6 | 258.4 | 300.2 | 232.8 | 236.8 | 241.6 | 269.6 |
| mean | 226.5$^d$ | 270.3$^b$ | 295.3$^a$ | 223.9$^d$ | 251.1$^c$ | 247.1$^c$ | 270.1$^b$ |
| g/c/d | 17.4 | 20.7 | 22.7 | 17.2 | 19.3 | 19.0 | 20.7 |

Pooled SEM = 4.6;
LSD = 13.5;
*chick removed or died;
g/c/d = grams/chick/day

| Feed Intake - 8-20 d (g) | | | | | | | |
|---|---|---|---|---|---|---|---|
| | 1 | 2 | 3 | 4 | 5 | 6 | 7 |
| R1 | 346.4 | 383.2 | 417.8 | 317.0 | 354.2 | 358.8 | 367.8 |
| R2 | 325.9* | 397.6 | 428.4 | 332.2 | 368.6 | 350.6 | 365.6* |
| R3 | 353.0 | 415.4 | 414.6 | 337.6 | 371.0 | 338.4 | 355.6 |
| R4 | 348.6 | 387.0 | 435.6 | 343.8 | 349.8 | 344.6 | 367.6 |
| mean | 343.4$^d$ | 395.8$^b$ | 424.1$^a$ | 332.6$^e$ | 360.9$^{cd}$ | 348.1$^{de}$ | 364.1$^c$ |
| g/c/d | 26.4 | 30.4 | 32.6 | 25.5 | 27.7 | 26.7 | 28.0 |

Pooled SEM = 5.3;
LSD = 15.6;
*chick removed or died

| Gain/Feed - 8-20 d (g) | | | | | | | |
|---|---|---|---|---|---|---|---|
| | 1 | 2 | 3 | 4 | 5 | 6 | 7 |
| R1 | 0.658 | 0.704 | 0.697 | 0.660 | 0.704 | 0.706 | 0.769 |
| R2 | 0.665* | 0.673 | 0.690 | 0.674 | 0.702 | 0.711 | 0.747* |
| R3 | 0.671 | 0.688 | 0.710 | 0.681 | 0.700 | 0.722 | 0.717 |
| R4 | 0.644 | 0.668 | 0.689 | 0.677 | 0.677 | 0.701 | 0.733 |
| mean | 0.659$^e$ | 0.683$^{cd}$ | 0.696$^{bc}$ | 0.673$^{de}$ | 0.695$^{bc}$ | 0.710$^b$ | 0.741$^a$ |

Pooled SEM = 0.006;
LSD = 0.020;
*chick removed or died

| Tibia Bone Ash (%) | | | | | | | |
|---|---|---|---|---|---|---|---|
| | 1 | 2 | 3 | 4 | 5 | 6 | 7 |
| R1 | 30.7 | 35.8 | 37.1 | 29.4 | 34.2 | 31.5 | 36.5 |
| R2 | 30.2* | 33.9 | 38.5 | 29.0 | 31.7 | 28.9 | 34.9* |
| R3 | 28.1 | 33.3 | 36.9 | 28.4 | 32.5 | 31.1 | 34.1 |
| R4 | 30.2 | 33.7 | 36.6 | 29.1 | 31.0 | 29.7 | 35.0 |
| mean | 29.8$^d$ | 34.1$^b$ | 37.2$^b$ | 28.9$^d$ | 32.3$^c$ | 30.3$^d$ | 35.1$^b$ |

Pooled SEM = 0.5;
LSD = 1.5;
*chick removed or died

| Tibia Bone Ash (g) | | | | | | | |
|---|---|---|---|---|---|---|---|
| | 1 | 2 | 3 | 4 | 5 | 6 | 7 |
| R1 | 0.242 | 0.318 | 0.427 | 0.215 | 0.262 | 0.283 | 0.338 |
| R2 | 0.230* | 0.312 | 0.418 | 0.232 | 0.296 | 0.250 | 0.345* |
| R3 | 0.239 | 0.327 | 0.394 | 0.233 | 0.270 | 0.253 | 0.327 |
| R4 | 0.241 | 0.300 | 0.390 | 0.248 | 0.254 | 0.261 | 0.339 |
| mean | 0.238$^e$ | 0.314$^c$ | 0.407$^a$ | 0.232$^e$ | 0.270$^d$ | 0.261$^d$ | 0.337$^b$ |

Pooled SEM = 0.006;
LSD = 0.019;
*chick removed or died

Slope ratio and standard curve analysis from the above results indicates that the low phytate corn contains 3 times more available phosphorus than in conventional corn.

EXAMPLE 3

The method of producing these elite, agronomically sound and high yielding mutants is a known method called mutagenesis. The process is outlined in the Neuffer paper Maize Genetic Newsletter 45:146. It should be noted that EMS is a mutation process. Like all mutation processes the act of mutation can adversely effect the agronomic traits especially yields of the plant. However, the starting germplasm is superior to that in which the phytate mutant was previously formed. Thus the overall agronomic traits of the plant of the present invention are more easily preserved and selected for then the industries approach of recurrent selection or backcrossing. Mutations were induced in the inbred line by treating pollen with ethyl methane sulfonate in paraffin oil according to the procedure described by Neuffer (1974). This treatment was performed on a number of inbreds from the various plant genotypes of cereal. This example will focus on the development of maize low-phytate mutants by this process. This mutagenesis process has been used to make a number of cereal mutants.

The general steps of the process of the present invention include treating inbred pollen (in this case maize) with ethyl methane sulfonate hereinafter "EMS". Inbred pollen is placed in EMS in oil for minutes. A paint brush is used and the pollen is brushed on to the silks of a receptive corn ear. This forms the Mutant-1 (M1) seed. Such seed are grown and self-pollinated to produce the Mutant-2 (M2) kernels. The resulting M2 kernels are tested for the low phytate phenotype.

EXAMPLE 4

The HVPE method is a common test for low phytate mutants, (Raboy, Mydica 35:383 (1990)). The method relies on differential migration of phosphorus compounds. After electrophoretically fractionating the compounds a chromatogram allows a semi quantitative assessment of the phytic acid relative to other compounds. An alternative method is screening for higher levels of inorganic P in the grain. For example grain samples can be ground (to pass a 2 mm screen in A Wiley mill) add either 50 mg of grain germ or 1 gram of endosperm in 15 ml of 0.4 M HCL in 0.7 $Na_2SO_4$. Phytic acid precipitates as an iron salt. Phosphorus in the ferric phytate precipitates and total P are determined. Phytic acid P (mg) are converted to phytic acid by conversion factor 3.5.

The principles of phytate measurement are known. In the method employed in the present study, a solution of 5-sulfosalicylic acid and $FeCl_3$ (Wade reagent) forms a pink chromophore. Phytic acid binds iron in this solution decreasing the level of the pink color. The measurement of this loss of color can be used as an indication of phytic acid levels. Since the blank contains no phytate, all readings of samples that do contain phytate will be negative numbers. If there is too much phytate, however, the iron-phytate complex can precipitate as a milky white substance. In this case the pink color will not be present but the milky white matter will absorb light and result in falsely high readings. Thus some visual observation may be necessary. This may necessitate using a smaller aliquot (less than 25 microliters) of the corn extract if the corn variety has high levels of phytate.

A rapid screening procedure, such as described as follows, may be used to score for putative low phytate seeds. In this procedure, a single edge razor is used to cut the kernel tip cap off just behind the black layer. The cut should transect the scutellum at a point at or near the radicle tip. Ususally, 8 representative kernels were selected from each ear. The kernels are then placed, cut surface up, on a microplate that has the surface covered with cellophane tape (sticky side up). The staining procedure was completed after dissection of at least 100 families.

Staining was done with the use of a repeating pipette to place a 10 microliter drop of Wade reagent (as described below) on the cut surface of each kernel. After a few minutes the color disappeared as the phytic acid from the scutellum binds the iron in the Wade reagent. Observations were made for families that segregate for slower disappearance of the pink color relative to the others (perhaps 5% of the total). These slower families were re-analyzed by the quantitative procedure described herein.

Phytate was quantified as follows. Individual kernels (7 to 10 from each family) were crushed in steel plate of a Carver hand-pump press (best results obtained when wells of plate lined with glycine paper and crushed with about 5000 lbs. pressure) and placed into 1.5 ml microcentrifuge tubes. 1 ml of 0.65 N hydrochloric acid was added and allowed to stand overnight. The combination was mixed by inversion the next day and allowed to settle for 5 minutes. A 15 microliter aliquot of the supernate was added to a microfuge tube with 100 microliters of buffer A (as described herein) and mixed. Low phytate mutants turn a very blue color due to the high phosphorus levels of the seeds. Mutants were generally retested the following day. The 0.65 N HCl extraction solution was made by adding 216 ml of 12.1N HCl to 3784 ml water. Reagent A was made fresh daily and included 2 parts (by volume) deionized water, 1 part (by volume) ascorbic acid solution, 1 part (by volume) ammonium molybdate solution and 1 part (by volume) $H_2SO_4$ solution. Ammonium molybdate solution was made by adding 25 g $(NH_4)_6MO_7O_{24} \times 4H_2O$ to make 1 L with water. $H_2SO_4$ solution was made by adding 167 ml of 36 N sulfuric acid to 833 ml water. Ascorbic acid solution was made by adding 100 g L-ascorbic acid to make 1 L with water. Ascorbic acid solution was stable with refrigeration for about seven weeks but only about two hours unrefrigerated.

Phytic Acid standards were prepared by means known in the art.

Maize kernel (M2) free phosphate was visually screened as follows. Kernels were selected, the phenotypes noted and placed in a multiple well crushing plate. Kernels were crushed in the multiple well crushing plate using a hydraulic press. Crushed kernels were transferred into 1.5 ml eppendorf microcentrifuge tubes. 0.5 ml of Reagent A was added. After allowing 2 hours reaction time, 0.5 ml reagent B was added. The tubes were capped and mixed by inverting. The reactions were scored visually for blueness after 1 hour, using a light box where necessary, and the bluest samples were selected as having highest phosphate. Often, the bluest samples from each family (ear) were selected and compared for final selection. Reagent A of this assay was prepared from 50 ml DMSO and 50 ml Reagent B. Reagent B was made fresh daily and prepared from 60 ml distilled water; 30 ml of 10% ascorbic solution (10 g ascorbic acid water to 100 ml total volume; the ascorbic solution was refrigerated and stable for 1 week); 30 ml of 3.5% ammonium molybdate solution (2.5 g $(NH4)_6 Mo_7O_{24}*4H_2O$ add water to 100 ml total volume); 30 ml of 6N sulfuric acid solution (170 ml water plus 25 ml concentrated $H_2SO_4$, adjust to 200 ml total volume with water).

Phytate (Red Test) was quantitatively measured as follows. Approximately 12 mature seeds were crushed in a steel crush plate of a Carver hand-pump press. Best results were obtained when wells of the plate were lined with weighing paper. Kernels were crushed with 5000 to 10000 lbs. pressure and transferred to Eppendorf tubes. 1 ml of 0.65 N HCl was added to same, allowed to sit overnight and mixed the following day by tube inversion. To assay, 200 µl of Wade-A reagent (described below) was combined with 10 µl of the above obtained corn/HCl juice extract in individual wells of a microtiter plate. Any change in color was noted and samples which remained red were noted as low in phytate since phytate binds with iron and turns the solution white. Quantitation may be completed with a spectrophotometer measuring at 490 nm. Wade-A reagent used herein was prepared by adding 25.4 g of 5-sulfosalicylic acid and 350 mg of $FeCl_3.6H_2O$ (ground with mortar and pestel if necessary) to 1.5 L deionized water. NaOH was used to adjust the pH to 3.05 and volume adjusted with $d.H_2O$ to 2 L. This reagent was stable in a refrigerator for about 1 mo. 0.65N HCl was prepared by adding 216 ml HCl (12. 1N) to 3784 ml of $d.H_2O$.

These assays allow the selection of the desired maize plants containing the desired alleles. Other methods of testing for phosphorus are known and can be used to select plants.

Seed containing the desired levels of phytic acid are then increased. This process was employed in the present invention and a number of inbred lines were selected that carried the low phytic acid mutation. These included several low phytate inbred lines with good combining ability which were crossed together to form a hybrid that produced the grain of the present invention. Thus, the developed inbreds of the present invention were produced from stiff stalk, Lancaster and another versatile heterotic patterns so that the inbreds when crossed together with the appropriate heterotic pattern formed excellent hybrid material. It was also discovered that a number of the developed mutations of the present invention though low in phytic acid were not the same mutant as the lpa1-R mutation. Additionally, the seed were screened for germinability in standard seed germination tests. It was found that some low phytate mutants were unable to germinate whereas others would germinate normally. Only the seed with good germination characteristics were maintained.

FIG. 1 shows an example of some data obtained form 3 such inbred lines screened for phytate content. Plotted as a frequency distribution curve it is clearly evident that there were a few samples with very low phytate content (less than 0.5 units (weight percent) whereas the bulk of the samples were higher in phytate content. The line known as UO95 line was selected as a starting material for its higher than average protein and oil levels. This line produces seed which are oil burdened and protein laden and which germinate normally. UO95py retains these characteristics with the low phytate levels described above. When crossed with certain other inbred lines, the resulting hybrid produces grain which are oil burdened and protein laden and contain low phytic levels.

The following table represents phytic acid contents (mg/g of seed) for mutant corn according to the present invention compared with wild-type seed.

| No. Seeds | Wild-type Line | Phytic acid | Mutant Line | Phytic acid | % reduction |
|---|---|---|---|---|---|
| 24 | UU01 | 1.16 | UU01-py | 0.17 | 85.3 |
| 12 | U095 | 1.85 | UO95-py | 0.14 | 92.4 |
| 12 | WD22 | 1.45 | WD22-py | 0.05 | 96.6 |

The following provides an example of an inbred line according to the present invention.

| Inbred | Protein | Oil | Phytate | % phytate reduction |
|---|---|---|---|---|
| Wild-type | | | | |
| UO95 | 13.4 | 606 | 1.85 | |
| UU01 | 12.7 | 2.9 | 1.16 | |
| B73 | 11.3 | 4.4 | — | |
| WD22 | — | — | 1.45 | |
| Mutants | | | | |
| UO95py | 14.4 | 5.3 | 0.14 | 85.3 |
| UU01py | 12.2 | 3.1 | 0.17 | 92.4 |
| B73lpa1-R | 13.2 | 3.2 | — | — |
| WD22py | — | — | 0.05 | 96.6 |

Protein and oil contents were measured by NIR analysis on a Dickey-John Reflectance Near Infra Red Spectrometer.

The grain of the present invention can also be used as a substitute source for the corn grain or flour used to make corn tortilla, corn meal, and cornflakes by substituting the grain of the present invention in the recipe and baking or processing as one would normally.

The grain of the present invention can also be used as a substitute for the corn wet milling industry by substituting the grain of the present invention in order to increase milling efficiency and recoverable starch content. Animal feed made as a by-product of the milling process is also substantially reduced in phytate content.

The entire contents of references referred to herein are incorporated in their entirety by reference.

We claim:

1. Seed of corn inbred line UO95py, representative seed of said line having been deposited under ATCC Accession No. 203034.

2. A hybrid corn seed produced by crossing corn inbred line UO95py with a second inbred corn line, wherein representative seed of said corn inbred line UO95py having been deposited under ATCC Accession No. 203034.

3. A corn plant, or parts thereof, produced by growing the seed of claim 1.

4. A corn plant, or parts thereof, produced by growing the seed of claim 2.

5. A method for producing a hybrid corn seed comprising crossing a first inbred parent corn plant with a second inbred parent corn plant and harvesting the resultant hybrid corn seed, wherein said first inbred parent corn plant or second said parent corn plant is the corn plant of claim 3.

6. A method for producing a UO95py-derived corn plant, comprising:
  a.) crossing inbred corn line UO95py, representative seed of said line having been deposited under ATCC Accession No. 203034, with a second corn plant to yield progeny corn seed; and
  b.) growing said progeny corn seed, under plant growth conditions, to yield said UO95py-derived corn plant.

7. A method for developing a corn plant in a corn plant breeding program using plant breeding techniques comprising employing a corn plant, or its parts, as a source of plant breeding material comprising: using the corn plant, or its parts, of claim 3 as a source of said breeding material.

* * * * *

UNITED STATES PATENT AND TRADEMARK OFFICE
CERTIFICATE OF CORRECTION

| | | |
|---|---|---|
| PATENT NO. | : 7,652,203 B2 | Page 1 of 1 |
| APPLICATION NO. | : 11/151129 | |
| DATED | : January 26, 2010 | |
| INVENTOR(S) | : Chang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1130 days.

Signed and Sealed this

Twenty-third Day of November, 2010

David J. Kappos
*Director of the United States Patent and Trademark Office*